United States Patent
Yamaji et al.

(10) Patent No.: US 11,046,665 B2
(45) Date of Patent: Jun. 29, 2021

(54) METHOD FOR PRODUCING α-HYDROXYCARBOXYLIC ACID DIMERIC CYCLIC ESTER

(71) Applicant: Kureha Corporation, Tokyo (JP)

(72) Inventors: Haruyasu Yamaji, Tokyo (JP); Yoshinori Suzuki, Tokyo (JP); Toshihiko Ono, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 16/476,908

(22) PCT Filed: Dec. 18, 2017

(86) PCT No.: PCT/JP2017/045359
§ 371 (c)(1),
(2) Date: Jul. 10, 2019

(87) PCT Pub. No.: WO2018/139107
PCT Pub. Date: Aug. 2, 2018

(65) Prior Publication Data
US 2019/0330175 A1    Oct. 31, 2019

(30) Foreign Application Priority Data

Jan. 24, 2017   (JP) .............. JP2017-010693

(51) Int. Cl.
| C07D 319/12 | (2006.01) |
| C08G 63/06 | (2006.01) |
| C08G 63/78 | (2006.01) |

(52) U.S. Cl.
CPC ........... *C07D 319/12* (2013.01); *C08G 63/06* (2013.01); *C08G 63/78* (2013.01)

(58) Field of Classification Search
CPC .................................................. C07D 319/12
See application file for complete search history.

(56) References Cited

U.S. PATENT DOCUMENTS

| 2,668,162 A | 2/1954 | Lowe |
| 5,830,991 A | 11/1998 | Shiiki et al. |
| 2003/0191326 A1 | 10/2003 | Yamane et al. |
| 2004/0087805 A1 | 5/2004 | Yamane et al. |
| 2004/0122240 A1 | 6/2004 | Yamane et al. |
| 2011/0155557 A1 | 6/2011 | Coszach et al. |
| 2014/0343298 A1 | 11/2014 | Yamaji et al. |
| 2016/0311793 A1 | 10/2016 | Penu et al. |

FOREIGN PATENT DOCUMENTS

| GB | 2331986 A | 6/1999 | |
| JP | 9-328481 A | * 12/1997 | |
| JP | H09328481 A | 12/1997 | |
| JP | 11255763 A | * 9/1999 | ........... C07D 319/12 |
| JP | H11255763 A | 9/1999 | |
| JP | 2004519485 A | 7/2004 | |
| JP | 2004523596 A | 8/2004 | |
| JP | 2010120915 A | * 6/2010 | |
| JP | 2010120915 A | 6/2010 | |
| JP | 2011506573 A | 3/2011 | |
| JP | 2017-500317 A | * 1/2017 | |
| JP | 2017500317 A | 1/2017 | |
| WO | WO0214303 A1 | 2/2002 | |
| WO | WO 2010/103884 A1 | 9/2010 | |
| WO | WO2013039038 A1 | 3/2013 | |

OTHER PUBLICATIONS

Office Action dated Apr. 7, 2020, in Japanese Patent Application No. 2018-564161.
International Search Report of the International Searching Authority for PCT/JP2017/045359 dated Feb. 6, 2018.
Translation of the International Search Report of the International Searching Authority for PCT/JP2017/045359 dated Feb. 6, 2018.
Written Opinion of the International Searching Authority for PCT/JP2017/045359 dated Feb. 6, 2018.
English translation of International Preliminary Report on Patentability and Written Opinion dated Aug. 8, 2019, in PCT/JP2017/045359 (Forms PCT/IB/338, PCT/IB/373, and PCT/ISA/237).

* cited by examiner

*Primary Examiner* — John S Kenyon
(74) *Attorney, Agent, or Firm* — Birch, Stewart, Kolasch & Birch, LLP

(57) ABSTRACT

Provided is a method for producing a high purity α-hydroxycarboxylic acid dimeric cyclic ester while heavy-component formation from an α-hydroxycarboxylic acid oligomer is suppressed. An α-hydroxycarboxylic acid dimeric cyclic ester is obtained by performing a depolymerization reaction in the coexistence of an inorganic acid or an inorganic acid salt or a mixture thereof; and an organophosphorus compound.

6 Claims, No Drawings

METHOD FOR PRODUCING α-HYDROXYCARBOXYLIC ACID DIMERIC CYCLIC ESTER

TECHNICAL FIELD

The present invention relates to a method for producing α-hydroxycarboxylic acid dimeric cyclic ester.

BACKGROUND ART

For a process of producing an α-hydroxycarboxylic acid dimeric cyclic ester, particularly for a process of depolymerizing an α-hydroxycarboxylic acid oligomer, development of a production method that can stabilize a reaction and that can produce a high purity α-hydroxycarboxylic acid dimeric cyclic ester has been demanded. Various studies have been thus conducted. For example, a method of controlling the heavy-component formation from an oligomer by adding a phenol-based antioxidant in a glycolide production process has been known (Patent Document 1).

Techniques related to this depolymerization process are also described in Patent Documents 2 and 3.

CITATION LIST

Patent Literature

Patent Document 1: WO 2013/039038
Patent Document 2: JP 11-255763 A
Patent Document 3: JP 2004-519485 T

SUMMARY OF INVENTION

Technical Problem

However, no significant effects have been achieved by the method described in Patent Document 1. Furthermore, α-hydroxycarboxylic acid, which is a raw material of the α-hydroxycarboxylic acid oligomer, may contain impurities such as alkali metal ions. When such a low purity raw material α-hydroxycarboxylic acid is used, problems occur in that byproducts in the α-hydroxycarboxylic acid dimeric cyclic ester increase over time during depolymerization and the purity declines over time, and the heavy-component formation from the oligomer becomes significant.

In order to solve the problems described above, an object of the present invention is to provide a method that can suppress production of byproducts and can produce a high purity α-hydroxycarboxylic acid dimeric cyclic ester over a longer period of time while heavy-component formation from an α-hydroxycarboxylic acid oligomer is suppressed, even when a low purity α-hydroxycarboxylic acid is used.

Solution to Problem

As a result of diligent research to achieve the object described above, the present inventors found that a high purity α-hydroxycarboxylic acid dimeric cyclic ester can be produced over a longer period of time by using a low purity α-hydroxycarboxylic acid as a raw material, while heavy-component formation from an α-hydroxycarboxylic acid oligomer is suppressed and production of byproducts is suppressed, by performing a depolymerization reaction of the α-hydroxycarboxylic acid oligomer in the coexistence of an inorganic acid or an inorganic acid salt or a mixture thereof; and an organophosphorus compound, and thus accomplished the present invention.

That is, the method for producing an α-hydroxycarboxylic acid dimeric cyclic ester according to an embodiment of the present invention (hereinafter, also referred to as "present production method") is a production method of obtaining an α-hydroxycarboxylic acid dimeric cyclic ester by subjecting an α-hydroxycarboxylic acid oligomer containing an alkali metal ion to a depolymerization reaction, and the depolymerization reaction is performed in the coexistence of an inorganic acid or an inorganic acid salt or a mixture thereof; and an organophosphorus compound.

Advantageous Effects of Invention

The present invention can produce a high purity α-hydroxycarboxylic acid dimeric cyclic ester over a longer period of time by using a low purity α-hydroxycarboxylic acid as a raw material, while heavy-component formation from an α-hydroxycarboxylic acid oligomer is suppressed.

DESCRIPTION OF EMBODIMENTS

Hereinafter, embodiments of the present invention will be described.

Method for Producing α-Hydroxycarboxylic Acid Dimeric Cyclic Ester

The method for producing an α-hydroxycarboxylic acid dimeric cyclic ester according to an embodiment of the present embodiment (hereinafter, also simply referred to as "present production method") is a method of obtaining an α-hydroxycarboxylic acid dimeric cyclic ester by subjecting an α-hydroxycarboxylic acid oligomer containing an alkali metal ion to a depolymerization reaction, and the depolymerization reaction is performed in the coexistence of an inorganic acid or an inorganic acid salt or a mixture thereof; and an organophosphorus compound.

α-Hydroxycarboxylic Acid Oligomer

The α-hydroxycarboxylic acid oligomer used in the present production method is produced by subjecting an α-hydroxycarboxylic acid, such as glycolic acid or lactic acid, to dehydration polycondensation.

The α-hydroxycarboxylic acid oligomer used in the present production method contains alkali metal ion(s). Note that, in the present embodiment, the alkali metal ion is not contained in a chain of an α-hydroxycarboxylic acid oligomer. Examples of such an alkali metal ion include a sodium ion, a lithium ion, a potassium ion, a rubidium ion, and a cesium ion. Among these, a large amount of sodium ions tends to be contained.

An α-hydroxycarboxylic acid (hereinafter, also referred to as "raw material α-hydroxycarboxylic acid"), which serves as a raw material for an α-hydroxycarboxylic acid oligomer, may contain alkali metal ions which originate from the production process of an α-hydroxycarboxylic acid and were not removed. When the concentration of the alkali metal ions in the depolymerization reaction system is high, progression of heavy-component formation from the α-hydroxycarboxylic acid oligomer during the depolymerization reaction or deterioration of the purity over time of the α-hydroxycarboxylic acid dimeric cyclic ester becomes significant. Because of this, the concentration of the alkali metal ions in the raw material α-hydroxycarboxylic acid is preferably as low as possible. However, complete removal of the alkali metal ion is typically not easy. Thus, in the present production method, the content of the alkali metal ion is preferably from 0.0001 wt. % to 1.0 wt. %, more preferably from 0.0001 wt. % to 0.01 wt. %, and even more preferably from 0.0001 wt. % to 0.001 wt. %, relative to the amount of the α-hydroxycarboxylic acid oligomer.

In order to reduce the negative effects of the alkali metal ions in the depolymerization reaction system described above, in the present production method, an inorganic acid or an inorganic acid salt or a mixture thereof is allowed to be present in the depolymerization reaction system, and a depolymerization reaction is performed in the coexistence of an inorganic acid or an inorganic acid salt or a mixture thereof; and the organophosphorus compound. Examples of the inorganic acid include sulfuric acid. Examples of the inorganic acid salt include iron sulfate, magnesium sulfate, nickel sulfate, copper sulfate, zinc sulfate, zirconium sulfate, and aluminum sulfate. Among these, iron sulfate is advantageous from the perspective of cost. Furthermore, when a mixture of an inorganic acid and an inorganic acid salt is used, the compounding ratio of these are not limited and may be set as appropriate.

The inorganic acid or the inorganic acid salt or the mixture thereof; and the organophosphorus compound are required to be present in the depolymerization reaction system. Examples of the method include a method of adding the inorganic acid or the inorganic acid salt or the mixture thereof; and the organophosphorus compound to a depolymerization reaction system containing an α-hydroxycarboxylic acid oligomer, and a method of allowing the α-hydroxycarboxylic acid oligomer to contain the inorganic acid or the inorganic acid salt or the mixture thereof; and the organophosphorus compound. To allow the glycolic acid oligomer to contain the inorganic acid or the inorganic acid salt or the mixture thereof; and the organophosphorus compound, there is a method of synthesizing an α-hydroxycarboxylic acid oligomer by adding the inorganic acid or the inorganic acid salt or the mixture thereof; and the organophosphorus compound to a raw material, such as an α-hydroxycarboxylic acid.

The amount of the inorganic acid or the inorganic acid salt or the mixture thereof present in the depolymerization reaction system is typically from 0.001 to 5 mass %, preferably from 0.01 to 3 mass %, and more preferably from 0.05 to 2 mass %. In many cases, long-term stabilization of the depolymerization reaction can be achieved by the presence of the inorganic acid or the inorganic acid salt or the mixture thereof in a proportion of from 0.05 to 0.5 mass % in the depolymerization reaction system.

When the amount of the alkali metal ions contained in the α-hydroxycarboxylic acid oligomer is known, the amount of the inorganic acid or the inorganic acid salt or the mixture thereof is adjusted to preferably from the equivalent amount (based on mass) to 100 times the equivalent amount, more preferably from 1.5 to 30 times the equivalent amount, and particularly preferably from 2 to 5 times the equivalent amount, of the alkali metal ions during the synthesis of the α-hydroxycarboxylic acid oligomer. When the content of the inorganic acid or the inorganic acid salt or the mixture thereof is too small, the long-term stabilization effect of the depolymerization reaction may be insufficient. On the other hand, when the content of the inorganic acid or the inorganic acid salt or the mixture thereof is too high, the long-term stabilization effect of the depolymerization reaction may be saturated, and increase in cost and in volume of the depolymerization reaction system may be caused. Furthermore, when the amount of the alkali metal ions contained in the α-hydroxycarboxylic acid oligomer is known, the inorganic acid or the inorganic acid salt or the mixture thereof may be added in a manner that the content thereof is the same as the amount ratio described above.

In the present specification, "oligomer" refers to an oligomer having a weight average molecular weight of approximately from 3000 to 20000.

The weighted average molecular weight of the α-hydroxycarboxylic acid oligomer in the present production method is typically 3000 or greater, preferably 5000 or greater, and more preferably 7000 or greater. The upper limit of the weight average molecular weight is typically approximately 20000 and in many cases approximately 15000. The weight average molecular weight is a value measured by using gel permeation chromatography (GPC).

The α-hydroxycarboxylic acid oligomer in the present production method is preferably a glycolic acid oligomer (hereinafter, also referred to as "GAO").

Commonly marketed technical grade glycolic acid contains approximately from 0.0001 wt. % to 1.0 wt. % of the alkali metal ions described above, such as sodium ions ($Na^+$). Therefore, in the present production method, an α-hydroxycarboxylic acid oligomer obtained by dehydration polycondensation of commercially available technical grade glycolic acid can be suitably used.

Note that the content of the alkali metals in the α-hydroxycarboxylic acid oligomer can be adjusted by a general method, such as an ion exchange membrane method or distillation purification.

Depolymerization of α-Hydroxycarboxylic Acid Oligomer Depolymerization Reaction

The method of depolymerizing the α-hydroxycarboxylic acid oligomer in the present production method is not particularly limited, and for example, a melt depolymerization method (document: U.S. Pat. No. 2,668,162 B), a solution depolymerization method (document: JP 9-328481 A and corresponding document: U.S. Pat. No. 5,830,911 B), a solid phase depolymerization method, and the like can be employed.

In the present production method, to stabilize the depolymerization reaction, the inorganic acid or the inorganic acid salt or the mixture thereof is allowed to exist in the depolymerization reaction system, and the depolymerization reaction is performed in the coexistence of this and the organophosphorus compound. As a result, even when a low purity α-hydroxycarboxylic acid raw material containing alkali metal ions or the like is used, the heavy-component formation from an α-hydroxycarboxylic acid oligomer and deterioration of the purity over time of the α-hydroxycarboxylic acid dimeric cyclic ester is suppressed, allowing depolymerization reaction to be performed stably for a longer period of time.

Examples of the organophosphorus compound include phosphoric acid ester compounds. Note that, in the present specification, "phosphoric acid ester compound" include phosphorous acid esters. Specific examples of the organophosphorus compound include triphenyl phosphite, tris(nonylphenyl)phosphite, tris(2,4-di-t-butylphenyl)phosphite, diphenyl isodecyl phosphite, phenyl diisodecyl phosphite, cyclic neopentane tetrayl bis(octadecylphosphite), cyclic neopentane tetrayl bis(2,6-di-t-butyl-4-methylphenyl)phosphite, 4,4'-butylidene-bis(3-methyl-6-t-butylphenylditridecyl)phosphite, 2,2-methylene bis(4,6-di-t-butylphenyl)octyl phosphite, mono(2-ethylhexyl)acid phosphate, monoisodecyl acid phosphate, monostearyl acid phosphate, monolauryl acid phosphate, monophenyl acid phosphate, di(2-ethylhexyl)acid phosphate, diisodecyl acid phosphate, distearyl acid phosphate, dilauryl acid phosphate, and diphenyl acid phosphate. Among these, from the perspective of thermal stability, cyclic neopentane tetrayl bis(2,6-di-t-butyl-4-methylphenyl) phosphite [CAS No. 80693-00-1; PEP-36, available from ADEKA), monostearyl acid phosphate, and distearyl acid phosphate are preferred. Note that, as an equimolar mixture of the monostearyl acid phosphate and the distearyl acid phosphate, there is AX-71, available from ADEKA.

In the present production method, the organophosphorus compound is preferably supplementarily added. At this time, the organophosphorus compound is preferably supplementarily added not earlier than the time when the purity of the α-hydroxycarboxylic acid dimeric cyclic ester in the depolymerization reaction decreases by 1 wt. %, more preferably by 1.2 wt. %, and even more preferably by 1.5 wt. %, compared to the purity at the time when the depolymerization reaction starts. The supplementary addition is effective for maintaining the effects of the organophosphorus compound addition for a longer period of time. The supplementary addition at the time prior to the decrease in the crude glycolide (GL) purity is not preferable from the perspective of maintaining the effect for a longer period of time because, in many cases, such supplementary addition is addition at the time prior to deterioration of the effect of the initially added organophosphorus compound. Thus, the addition not earlier than the time when the purity decrease described above is observed is preferred.

Accordingly, in the present production method, the organophosphorus compound may be (i) added at initiation of the depolymerization reaction or in a step prior to the initiation and supplementarily added at the timing described above after the initiation of the depolymerization reaction. Alternatively, the organophosphorus compound may be (ii) supplementarily added stepwise at the timing described above after the initiation of the depolymerization reaction.

Furthermore, when the supplementary addition is performed a plurality of times, the number of such addition may be selected depending on the condition of the depolymerization reaction; however, the total amount of the added organophosphorus compound is from 0.01 wt. % to 2.0 wt. % relative to the amount of the depolymerization reaction solution.

In the present production method, a solvent is preferably used to improve the depolymerization reactivity of the α-hydroxycarboxylic acid oligomer. The solvent is preferably a polar organic solvent and more preferably a high-boiling-point polar organic solvent having a boiling point of from 230 to 450° C. Such a high-boiling-point polar organic solvent acts as a solvent in the depolymerization reaction and acts as a codistillation component when a produced α-hydroxycarboxylic acid dimeric cyclic ester is removed from the reaction system, and it is possible to prevent the α-hydroxycarboxylic acid dimeric cyclic ester or the like from adhering to the inner wall of the production line. That is, by setting the boiling point of the polar organic solvent to be within the range described above, the depolymerization reaction temperature can be set to be high, and the production rate of the α-hydroxycarboxylic acid dimeric cyclic ester can be set to be high. Furthermore, when the boiling point of the polar organic solvent is within the range described above, the codistillation of the polar organic solvent and the produced α-hydroxycarboxylic acid dimeric cyclic ester during the depolymerization reaction is facilitated. From this perspective, the boiling point of the high-boiling-point polar organic solvent is more preferably from 235 to 450° C., even more preferably from 255 to 430° C., and particularly preferably from 280 to 420° C. Note that, in the present embodiment, the boiling point of the polar organic solvent is a value at normal pressure, and when the boiling point is measured under reduced pressure, the boiling point of the polar organic solvent is converted to a value at normal pressure.

Furthermore, the molecular weight of such a polar organic solvent is preferably from 150 to 450, more preferably from 180 to 420, and particularly preferably from 200 to 400. The molecular weight of the polar organic solvent within the range described above facilitates the occurrence of codistillation with the glycolide.

Examples of the high-boiling-point polar organic solvent include aromatic dicarboxylic acid diesters, aromatic carboxylic acid esters, aliphatic dicarboxylic acid diesters, polyalkylene glycol diethers, aromatic dicarboxylic acid dialkoxyalkyl esters, aliphatic dicarboxylic acid dialkoxyalkyl esters, polyalkylene glycol diesters, and aromatic phosphoric acid esters. Among these high-boiling-point polar organic solvents, aromatic dicarboxylic acid diesters, aromatic carboxylic acid esters, aliphatic dicarboxylic acid diesters, and polyalkylene glycol diethers are preferred. From the perspective of being less likely to cause thermal degradation, a polyalkylene glycol diether is more preferable. One type of the high-boiling-point polar organic solvents may be used alone, or two or more types of the high-boiling-point polar organic solvents may be used in combination.

Examples of the aromatic dicarboxylic acid diester include phthalic acid esters, such as dibutyl phthalate, dioctyl phthalate, dibenzyl phthalate, and benzyl butyl phthalate. Examples of the aromatic carboxylic acid ester include benzoic acid esters, such as benzyl benzoate. Examples of the aliphatic dicarboxylic acid diesters include adipic acid esters, such as dioctyl adipate, and sebacic acid esters, such as dibutyl sebacate.

Examples of the polyalkylene glycol diether include compounds represented by Formula (1) below:

$$X^1-O-(R^1-O)_p-Y^1 \qquad (1)$$

In Formula (1) above, $R^1$ represents a methylene group or a straight or branched alkylene group having from 2 to 8 carbons, $X^1$ represents a hydrocarbon group, and $Y^1$ represents an alkyl group having from 2 to 20 carbons or an aryl group having from 6 to 20 carbons. p is an integer of 1 or greater, and when p is 2 or greater, a plurality of $R^1$ moieties may be the same or different.

$R^1$ in Formula (1) above is not particularly limited as long as $R^1$ is a methylene group or a straight or branched alkylene group having from 2 to 8 carbons but is preferably an ethylene group from the perspective of ease in acquisition or synthesis of the polyalkylene glycol diether represented by Formula (1) above.

$X^1$ in Formula (1) above is a hydrocarbon group, such as an alkyl group or an aryl group and, among these, is preferably a hydrocarbon group having from 1 to 20 carbons. When the number of carbons in the hydrocarbon group exceeds the upper limit described above, the polarity of the polyalkylene glycol diether represented by Formula (1) above decreases, the solubility of the α-hydroxycarboxylic acid oligomer decreases, and the codistillation with the α-hydroxycarboxylic acid dimeric cyclic ester tends to be difficult. Examples of the alkyl group include a methyl group, an ethyl group, a propyl group, a butyl group, a pentyl group, a hexyl group, a heptyl group, an octyl group, a nonyl group, a decyl group, and a lauryl group. These alkyl groups may be straight-chained or branched-chained. Examples of the aryl group include a phenyl group, a naphthyl group, a substituted phenyl group, and a substituted naphthyl group.

The substituent of the substituted phenyl group and the substituted naphthyl group is preferably an alkyl group, an alkoxy group, or a halogen atom (Cl, Br, I, or the like). The number of such substituents is, for example, from 1 to 5 in the case of a substituted phenyl group and preferably from 1 to 3. In the case where a plurality of substituents are present, the substituents may be the same or different. Note that such a substituent serves to adjust the boiling point and the polarity of the polyalkylene glycol diether.

In Formula (1) above, $Y^1$ is an alkyl group having from 2 to 20 carbons or an aryl group having from 6 to 20 carbons. The number of carbons of $Y^1$ within the range described above can prevent the polarity of the polyalkylene glycol diether represented by Formula (1) above from decreasing, thus can prevent the solubility of the α-hydroxycarboxylic acid oligomer from decreasing, and can facilitate the codistillation with the α-hydroxycarboxylic acid dimeric cyclic ester. When $Y^1$ is a methyl group, the number of carbons of $R^1$ needs to be increased because the polyalkylene glycol diether represented by Formula (1) above is a solvent with a high boiling point appropriate for codistillation with an α-hydroxycarboxylic acid dimeric cyclic ester. However, when such a polyalkylene glycol diether is synthesized, p in Formula (1) above has a wide distribution, and production process becomes complicated because of needs for purification by distillation or the like. Therefore, from the perspective of performing on a technical scale, a polyalkylene glycol diether in which $Y^1$ in Formula (1) above is a methyl group is not preferred. Examples of the alkyl group and the aryl group include those exemplified as the alkyl group and the aryl group of $X^1$ above.

In Formula (1) above, p is an integer of 1 or greater but is preferably an integer of 2 or greater. On the other hand, the upper limit of p is not particularly limited, but p is preferably an integer of 8 or less and more preferably an integer of 5 or less. When p exceeds the upper limit described above, the distribution of the degree of polymerization becomes wider during the synthesis of the polyalkylene glycol diether, and the polyalkylene glycol diether having the same p in Formula (1) above is less likely to be isolated. Furthermore, when p is 2 or greater, the plurality of $R^1$ moieties may be the same or different.

Among such polyalkylene glycol diethers, a polyalkylene glycol diether in which both X' and Y' in Formula (1) above are each an alkyl group and the sum of the carbons of X' and Y' is from 3 to 21 (more preferably from 6 to 20) is preferred. Furthermore, in this case, X' and Y' may be alkyl groups that are the same or different.

Specific examples of such a polyalkylene glycol diether include:

polyethylene glycol dialkyl ethers, such as diethylene glycol dibutyl ether, diethylene glycol dihexyl ether, diethylene glycol dioctyl ether, diethylene glycol butyl-2-chlorophenyl ether, triethylene glycol diethyl ether, triethylene glycol dipropyl ether, triethylene glycol dibutyl ether, triethylene glycol dihexyl ether, triethylene glycol dioctyl ether, triethylene glycol butyloctyl ether, triethylene glycol butyldecyl ether, tetraethylene glycol diethyl ether, tetraethylene glycol dipropyl ether, tetraethylene glycol dibutyl ether, tetraethylene glycol dihexyl ether, tetraethylene glycol dioctyl ether, diethylene glycol butylhexyl ether, diethylene glycol butyloctyl ether, diethylene glycol hexyloctyl ether, triethylene glycol butylhexyl ether, triethylene glycol hexyloctyl ether, tetraethylene glycol butylhexyl ether, tetraethylene glycol butyloctyl ether, and tetraethylene glycol hexyloctyl ether;

polyalkylene glycol dialkyl ethers each having a propylene oxy group or a butylene oxy group in place of the ethylene oxy group of each of these polyethylene glycol dialkyl ethers described above (e.g. polypropylene glycol dialkyl ether and polybutylene glycol dialkyl ether);

polyethylene glycol alkylaryl ethers, such as diethylene glycol butylphenyl ether, diethylene glycol hexylphenyl ether, diethylene glycol octylphenyl ether, triethylene glycol butylphenyl ether, triethylene glycol hexylphenyl ether, triethylene glycol octylphenyl ether, tetraethylene glycol butylphenyl ether, tetraethylene glycol hexylphenyl ether, tetraethylene glycol octylphenyl ether, and a compound in which a hydrogen atom of the phenyl group in each of these polyethylene glycol alkylphenyl ethers is substituted with an alkyl group, an alkoxy group, a halogen atom, or the like;

polyalkylene glycol alkylaryl ethers each having a propylene oxy group or a butylene oxy group in place of the ethylene oxy group of each of these polyethylene glycol alkylaryl ethers (e.g. polypropylene glycol alkylaryl ether and polybutylene glycol alkylaryl ether);

polyethylene glycol diaryl ethers, such as diethylene glycol diphenyl ether, triethylene glycol diphenyl ether, tetraethylene glycol diphenyl ether, and a compound in which a hydrogen atom of the phenyl group in each of these polyethylene glycol diphenyl ethers is substituted with an alkyl group, an alkoxy group, a halogen atom, or the like; and polyalkylene glycol diaryl ethers each having a propylene oxy group or a butylene oxy group in place of the ethylene oxy group of each of these polyethylene glycol diaryl ethers (e.g. polypropylene glycol diaryl ether and polybutylene glycol diaryl ether).

Furthermore, such polyalkylene glycol diethers can be synthesized by the method described in the document of WO 02/014303.

Among these polyalkylene glycol diethers, a polyalkylene glycol dialkyl ether is preferred, and diethylene glycol dialkyl ether, triethylene glycol dialkyl ether, and tetraethylene glycol dialkyl ether are more preferred from the perspectives of being easy to synthesize and being less likely to cause thermal degradation.

Furthermore, the polyalkylene glycol diether used in the present production method is preferably a polyalkylene glycol diether having a solubility of the α-hydroxycarboxylic acid dimeric cyclic ester of from 0.1 to 10% at 25° C. Note that the solubility of the α-hydroxycarboxylic acid dimeric cyclic ester represents a percentage of the mass (g) of the α-hydroxycarboxylic acid dimeric cyclic ester relative to the volume (mL) of the polyalkylene glycol diether at the time when the α-hydroxycarboxylic acid dimeric cyclic ester is dissolved to saturation in the polyalkylene glycol diether at 25° C. When the solubility of the α-hydroxycarboxylic acid dimeric cyclic ester is less than the lower limit described above, the α-hydroxycarboxylic acid dimeric cyclic ester codistilled with the polyalkylene glycol diether tends to precipitate in the middle of the production line, and clogging of the production line or the like tends to occur. On the other hand, when the solubility of the α-hydroxycarboxylic acid dimeric cyclic ester exceeds the upper limit described above, to recover the codistilled α-hydroxycarboxylic acid dimeric cyclic ester, for example, the codistillation product may need to be cooled to 0° C. or lower, or the α-hydroxycarboxylic acid dimeric cyclic ester may need to be isolated by addition of a poor solvent to the codistillation product.

Examples of the polyalkylene glycol diether having the α-hydroxycarboxylic acid dimeric cyclic ester solubility specified as described above include tetraethylene glycol dibutyl ether (boiling point=340° C., molecular weight=306, solubility of glycolide=4.6%), triethylene glycol butyloctyl ether (boiling point=350° C., molecular weight=350, solubility of glycolide=2.0%), triethylene glycol butyldecyl ether (boiling point=400° C., molecular weight=400, solubility of glycolide=1.3%), diethylene glycol dibutyl ether (boiling point=256° C., molecular weight=218, solubility of glycolide=1.8%), and diethylene glycol butyl-2-chlorophenyl ether (boiling point=345° C., molecular weight=273, solubility of glycolide=1.8%). Among these, from the perspectives of ease in synthesis, thermal degradation resistance, depolymerization reactivity of the α-hydroxycarboxylic acid oligomer, and recoverability of the α-hydroxycarboxylic acid dimeric cyclic ester, tetraethylene glycol dibutyl ether and triethylene glycol butyloctyl ether are more preferred.

In the present production method, the amount of the solvent in the reaction system is preferably from 30 to 5000 parts by mass, more preferably from 50 to 2000 parts by mass, and particularly preferably from 60 to 200 parts by mass, per 100 parts by mass of the α-hydroxycarboxylic acid oligomer. When the amount of the solvent is less than the lower limit described above, the ratio of the solution phase of the α-hydroxycarboxylic acid oligomer in the reaction system tends to decrease under depolymerization temperature conditions (increasing the ratio of the melt phase of the α-hydroxycarboxylic acid oligomer), and the depolymerization reactivity of the α-hydroxycarboxylic acid oligomer tends to decrease; or heavy-component tends to be formed from an α-hydroxycarboxylic acid oligomer in the melt phase. On the other hand, when the amount of the solvent exceeds the upper limit described above, the thermal efficiency during the depolymerization reaction tends to decrease, and the productivity of the α-hydroxycarboxylic acid dimeric cyclic ester due to the depolymerization reaction tends to decrease.

Solubilizing Agent

In the present embodiment, a solubilizing agent is preferably added to enhance the dissolution characteristics (solubility and/or dissolution rate) of the α-hydroxycarboxylic acid oligomer in the solvent described above (especially, high-boiling-point polar organic solvent). Furthermore, the depolymerization reactivity of the α-hydroxycarboxylic acid oligomer can be increased by adding a solubilizing agent. Such a solubilizing agent is preferably a compound which satisfies at least one of the following requirements (1) to (4).

(1) Being a non-basic compound. Examples of the non-basic compound include a compound having a functional group, such as an OH group, a COOH group, a CONH group, or the like. Basic compounds, such as amines, pyridines, and quinolines, are not preferable because the basic compounds may react with the α-hydroxycarboxylic acid oligomer and/or the α-hydroxycarboxylic acid dimeric cyclic ester that is produced.

(2) Being a compound that is miscible with or soluble in the solvent. The compound may be a liquid or a solid at room temperature as long as the compound is miscible with or soluble in the solvent.

(3) Being a compound having a boiling point of 180° C. or higher, preferably 200° C. or higher, more preferably 230° C. or higher, and particularly preferably 250° C. or higher. In particular, the use of a compound having a higher boiling point than the boiling point of the solvent used in the depolymerization reaction as a solubilizing agent is preferable because the solubilizing agent does not distill out when the α-hydroxycarboxylic acid dimeric cyclic ester and the solvent are codistilled or the distilled amount thereof becomes extremely low. In many cases, using a compound having a boiling point of 450° C. or higher as a solubilizing agent can achieve good results in which the solubilizing agent does not distill out or in which the amount of distillation is extremely low. However, in the case of alcohols and the like, even a compound with a lower boiling point than the boiling point of the solvent used in the depolymerization reaction can be suitably used as a solubilizing agent.

(4) Having a higher affinity with the α-hydroxycarboxylic acid oligomer than that with the solvent. Note that the affinity of the solubilizing agent and the α-hydroxycarboxylic acid oligomer can be confirmed by forming a uniform solution phase by heating a mixture of the α-hydroxycarboxylic acid oligomer and the solvent to a temperature of 230° C. or higher, further adding the α-hydroxycarboxylic acid oligomer therein to increase the concentration thereof until the mixture does not form a uniform solution phase, then adding a solubilizing agent therein, and visually observing whether a uniform solution phase is formed again.

In the production method, a compound satisfying any one or more of these requirements is preferably used as the solubilizing agent. Specifically, having a boiling point of 180° C. or higher, more preferably 200° C. or higher, even more preferably 230° C. or higher, and particularly preferably 250° C. or higher, at least one type of non-basic organic compound that is selected from the group consisting of alcohols; phenols; aliphatic carboxylic acids; aliphatic amides; aliphatic imides; polyalkylene glycol diethers having a molecular weight of greater than 450; and sulfonic acids is preferably used as the solubilizing agent.

Among such solubilizing agents, alcohols are particularly effective. Examples of the alcohols include aliphatic alcohols, such as decanol, tridecanol, decanediol, ethylene glycol, propylene glycol, and glycerin; aromatic alcohols, such as cresol, chlorophenol, and naphthyl alcohol; polyalkylene glycols; and polyalkylene glycol monoethers. One type of these alcohols may be used alone, or two or more types of these alcohols may be used in combination.

Furthermore, among such alcohols, a polyalkylene glycol monoether represented by Formula (2) below is preferred because almost no such a polyalkylene glycol monoether distills out due to its high boiling point, and the polyalkylene glycol monoether has high solubility of the α-hydroxycarboxylic acid oligomer, promotes depolymerization reaction, and exhibits excellent cleaning effect of the inner wall of a reactor.

$$HO-(R^2-O)_q-X^2 \qquad (2)$$

In Formula (2), $R^2$ represents a methylene group or a straight or branched alkylene group having from 2 to 8 carbons, and $X^2$ represents a hydrocarbon group. q is an integer of 1 or greater. In the case where q is 2 or greater, a plurality of the $R^2$ moieties may be the same or different.

The $R^2$ in Formula (2) above is not particularly limited as long as $R^2$ is a methylene group or a straight or branched alkylene group having from 2 to 8 carbons. However, $R^2$ is preferably an ethylene group from the perspective of ease in acquisition or synthesis of the polyalkylene glycol diether represented by Formula (2) above. Furthermore, $X^2$ in Formula (2) above is a hydrocarbon group, such as an alkyl group or an aryl group and, among these, is preferably a hydrocarbon group having from 1 to 18 carbons, and more preferably a hydrocarbon group having from 6 to 18 carbons.

Among such polyalkylene glycol monoethers, polyethylene glycol monoalkyl ethers, such as polyethylene glycol monomethyl ether, polyethylene glycol monoethyl ether, polyethylene glycol monopropyl ether, polyethylene glycol monobutyl ether, polyethylene glycol monohexyl ether, polyethylene glycol monooctyl ether, polyethylene glycol monodecyl ether, and polyethylene glycol monolauryl ether; and polyalkylene glycol monoalkyl ethers each having a propylene oxy group or a butylene oxy group in place of the ethylene oxy group of each of these polyethylene glycol monoalkyl ether (e.g. polypropylene glycol monoalkyl ether and polybutylene glycol monoalkyl ether) are preferred. Polyethylene glycol monohexyl ether, polyethylene glycol monooctyl ether, polyethylene glycol monodecyl ether, and polyethylene glycol monolauryl ether; and polyalkylene glycol monoethers each having a propylene oxy group or a butylene oxy group in place of the ethylene oxy group of each of these polyethylene glycol monoalkyl ether are more preferred. One type of these polyalkylene glycol monoethers may be used alone, or two or more types of these polyalkylene glycol monoethers may be used in combination.

Furthermore, other preferred alcohols include polyalkylene glycols represented by Formula (3) below.

$$\text{HO}-(\text{R}^3-\text{O})_r-\text{H} \qquad (3)$$

In Formula (3), $R^3$ represents a methylene group or a straight or branched alkylene group having from 2 to 8 carbons. r is an integer of 1 or greater, and when r is 2 or greater, a plurality of $R^3$ moieties may be the same or different.

$R^3$ in Formula (3) above is not particularly limited as long as $R^3$ is a methylene group or a straight or branched alkylene group having from 2 to 8 carbons but is preferably an ethylene group from the perspective of ease in acquisition or synthesis of the polyalkylene glycol represented by Formula (3) above.

Examples of such a polyalkylene glycol include polyethylene glycol, polypropylene glycol, and polybutylene glycol. One type of these polyalkylene glycols may be used alone, or two or more types of these polyalkylene glycols may be used in combination.

Furthermore, examples of polyalkylene glycol diether which can be used as the solubilizing agent and has a molecular weight of greater than 450 include polyethylene glycol dimethyl ether #500 (average molecular weight: 500) and polyethylene glycol dimethyl ether #2000 (average molecular weight: 2000). When the molecular weight is less than or equal to the lower limit described above, the solubilizing agent is also distilled out together with the distillation of the α-hydroxycarboxylic acid dimeric cyclic ester during the depolymerization reaction, and the solubility of the α-hydroxycarboxylic acid oligomer in the mixture according to the present embodiment tends to decrease.

Note that the action of the solubilizing agent in the depolymerization reaction of the α-hydroxycarboxylic acid oligomer is not yet sufficiently apparent. However, the present inventors hypothesize as described below. That is, the solubilizing agent is assumed to exhibit 1) action to change the condition of the α-hydroxycarboxylic acid oligomer to a condition that is easily dissolved by reacting with a terminal of the α-hydroxycarboxylic acid oligomer, 2) action to change the α-hydroxycarboxylic acid oligomer to a substance that is easily dissolved by cutting the molecular chain by action to a middle of the molecular chain of the α-hydroxycarboxylic acid oligomer and adjusting the molecular weight, 3) action to enhance solubility of the α-hydroxycarboxylic acid oligomer by changing the polarity of the entire solvent system to enhance affinity, 4) action to emulsify and disperse the α-hydroxycarboxylic acid oligomer, 5) action to increase the depolymerization reaction points by bonding to one terminal of the α-hydroxycarboxylic acid oligomer, and 6) action to cut the molecular chain by action to a middle of the α-hydroxycarboxylic acid oligomer and increase the depolymerization reaction points by bonding to the cut molecular chain terminal or is assumed to perform 7) a combination of these actions.

In the present production method, the amount of the solubilizing agent in the reaction system is preferably from 0.1 to 500 parts by mass and more preferably from 1 to 300 parts by mass, per 100 parts by mass of the α-hydroxycarboxylic acid oligomer. When the amount of the solubilizing agent is less than the lower limit described above, the solubility characteristics of the α-hydroxycarboxylic acid oligomer with respect to the solvent (particularly, the high-boiling-point polar organic solvent) may decrease. On the other hand, when the content of the solubilizing agent exceeds the upper limit described above, recovery of the solubilizing agent is costly, and such content tends to be unfavorable in terms of economic efficiency.

Method for producing α-hydroxycarboxylic acid dimeric cyclic ester Hereinafter, a method for depolymerizing an α-hydroxycarboxylic acid oligomer in a solvent in the coexistence of an inorganic acid or an inorganic acid salt or a mixture thereof; and an organophosphorus compound will be described in detail.

Dissolution Step

First, an α-hydroxycarboxylic acid oligomer, a solvent, a solubilizing agent, and an organophosphorus compound are mixed in the presence of an inorganic acid or an inorganic acid salt or a mixture thereof. Note that the inorganic acid or the inorganic acid salt or the mixture thereof as well as the organophosphorus compound need to be present in the reaction solution during the depolymerization reaction as described above, and the addition timing may be any of the depolymerization reaction step, the dissolution step, or the addition to the raw material α-hydroxycarboxylic acid.

The resulting mixture is heated to dissolve the α-hydroxycarboxylic acid oligomer in the solvent, thus forming a uniform solution phase. At this time, a solubilizing agent is preferably mixed into this mixture. As a result, the solubility of the α-hydroxycarboxylic acid oligomer in the solvent is enhanced, and the production and volatilization rate of the α-hydroxycarboxylic acid dimeric cyclic ester can be dramatically enhanced.

At this time, the heating temperature of the mixture is preferably from 200 to 350° C., more preferably from 210 to 310° C., even more preferably from 220 to 300° C., and particularly preferably from 230 to 290° C. When the heating temperature is within this range, the α-hydroxycarboxylic acid oligomer is efficiently dissolved in a solvent, and a uniform solution is obtained. Furthermore, it is possible to suppress heavy-component formation from the t-hydroxycarboxylic acid oligomer.

The heating of the mixture may be performed at ambient pressure or under reduced pressure; however, the heating of the mixture is preferably performed at from 0.1 kPa to 90 kPa, preferably from 1 kPa to 30 kPa, and more preferably from 2 kPa to 10 kPa. Furthermore, heating in an inert gas atmosphere is preferred.

Depolymerization Step

The solution phase prepared as described above (i.e. a phase in which the α-hydroxycarboxylic acid oligomer, the organophosphorus compound, and, as necessary, the solvent and the solubilizing agent are substantially uniformly dissolved in the solvent) is then further heated to depolymerize the α-hydroxycarboxylic acid oligomer in this solution phase, and thus an α-hydroxycarboxylic acid dimeric cyclic ester is produced.

In the present production method, the depolymerization reaction is performed in the coexistence of the inorganic acid or the inorganic acid salt or the mixture thereof; and the organophosphorus compound. As a result, heavy-component formation from the α-hydroxycarboxylic acid oligomer and the deterioration of the purity over time of the α-hydroxycarboxylic acid dimeric cyclic ester are suppressed.

Preferred conditions such as temperature and pressure in the depolymerization reaction are the same as the preferred conditions in the dissolution step described above. Furthermore, the heating conditions in the dissolution step and the heating conditions in the depolymerization step may be the same or different. In particular, the pressure is preferably low from the perspectives of reducing the depolymerization reaction temperature and capability of suppressing thermolysis of the α-hydroxycarboxylic acid oligomer, and typically, the heating is performed at a pressure equal to or lower than the pressure in the dissolution step.

In the present production method, in the depolymerization reaction, preferably from 0.01 wt. % to 2.0 wt. %, more preferably from 0.05 wt. % to 1.5 wt. %, and even more preferably from 0.1 wt. % to 1.0 wt. % of the organophosphorus compound is contained relative to the amount of the reaction solution.

Distillation Step

Next, the α-hydroxycarboxylic acid dimeric cyclic ester produced as described above is distilled out together with the solvent. As a result, the attachment of the α-hydroxycarboxylic acid dimeric cyclic ester to the inner wall of the production line is suppressed, and clogging of the line can be prevented. Furthermore, this depolymerization reaction is a reversible reaction. Therefore, by distilling the α-hydroxycarboxylic acid dimeric cyclic ester from the reaction system, the depolymerization reaction of the α-hydroxycarboxylic acid oligomer proceed efficiently.

In the case where the α-hydroxycarboxylic acid dimeric cyclic ester is continuously produced by the present production method, α-hydroxycarboxylic acid oligomer in an amount corresponding to the distilled amount of the α-hydroxycarboxylic acid oligomer is preferably continuously or intermittently replenished into the depolymerization reaction system. At this time, it is necessary to replenish the α-hydroxycarboxylic acid oligomer so that the condition in which the α-hydroxycarboxylic acid oligomer is uniformly dissolved in the solvent is maintained.

Recovering Step

The α-hydroxycarboxylic acid dimeric cyclic ester that is distilled out together with the solvent in this manner can be recovered by the method described in the document: JP 2004-523596 A or the document: WO 02/014303. For example, the α-hydroxycarboxylic acid dimeric cyclic ester can be recovered by cooling the codistillation product of the α-hydroxycarboxylic acid dimeric cyclic ester and the solvent and, as necessary, adding a poor solvent to solidify and/or precipitate. Furthermore, in the case where a solvent having excellent thermal stability is used as described in the document: WO 02/014303, the α-hydroxycarboxylic acid dimeric cyclic ester can be recovered by phase separation.

Method for Producing Polyglycolic Acid

The method for producing a polyglycolic acid according to the present embodiment includes the method for producing an α-hydroxycarboxylic acid dimeric cyclic ester described above. In the method for producing a polyglycolic acid, the α-hydroxycarboxylic acid dimeric ester obtained by the present production method needs to be subjected to ring-opening polymerization.

The ring-opening of the α-hydroxycarboxylic acid dimeric ester may be performed by a known method.

Summary

The method for producing an α-hydroxycarboxylic acid dimeric cyclic ester according to an embodiment of the present invention (hereinafter, also referred to as "present production method") includes subjecting an α-hydroxycarboxylic acid oligomer containing an alkali metal ion to a depolymerization reaction to obtain an α-hydroxycarboxylic acid dimeric cyclic ester, and the depolymerization reaction is performed in the coexistence of an inorganic acid or an inorganic acid salt or a mixture thereof; and an organophosphorus compound.

In the present production method, the organophosphorus compound is preferably added in an amount of from 0.01 wt. % to 2.0 wt. % relative to the amount of a reaction solution in the depolymerization reaction.

In the present production method, the organophosphorus compound is preferably supplementarily added.

In the present production method, in the depolymerization reaction, the organophosphorus compound is preferably supplementarily added not earlier than the time when the purity of the α-hydroxycarboxylic acid dimeric cyclic ester decreases by 1% compared to purity at the time when the reaction starts.

In the present production method, the content of the alkali metal ion is preferably from 0.0001 wt. % to 1.0 wt. % relative to the amount of the α-hydroxycarboxylic acid oligomer.

In the present production method, the organophosphorus compound is preferably a phosphoric acid ester compound. Note that the phosphoric acid ester compound herein include phosphorous acid ester compounds.

In the present production method, the α-hydroxycarboxylic acid oligomer is preferably a glycolic acid oligomer.

The present invention also provides a method for producing a polyglycolic acid. This method for producing a polyglycolic acid includes the method for producing an α-hydroxycarboxylic acid dimeric cyclic ester described above.

The present invention is not limited to the embodiments described above, and various modifications are possible within the scope indicated in the claims. Embodiments obtained by appropriately combining the technical means disclosed by other embodiments are also included in the technical scope of the present invention.

EXAMPLES

The present invention will be described in further detail hereafter based on the examples and comparative example, but the present invention is not limited to the following examples.

Preparation Example 1

In an autoclave having the volume of 20 L, 20 kg of a technical grade 70 wt. % glycolic acid aqueous solution (available from DuPont) was charged. Note that, the technical grade glycolic acid aqueous solution that was used contained 330 ppm of $Na^+$ as an alkali metal ion, which was an impurity. To reduce the effect of the alkali metal ion, 25.3 g of iron(III) sulfate nonahydrate was also charged together. Next, the mixture was heated at normal pressure to increase the temperature from 25° C. to 210° C. while being stirred. During this time, a polycondensation reaction was performed while the generated water was distilled off. Next, the pressure in the autoclave was gradually reduced from ambient pressure to 3 kPa over 1 hour, then heating was performed at 210° C. for 3 hours to continue dehydration polycondensation reaction, and a glycolic acid oligomer (TGAO) was obtained. The melting point of this glycolic acid oligomer was 215° C.

Example 1

In a container having the volume of 0.5 L, 126 g of the glycolic acid oligomer (TGAO) obtained in Preparation Example 1, 130 g of tetraethylene glycol dibutyl ether (TEG-DB) as a solvent, 100 g of polyethylene glycol monooctyl ether (OTeG) as a solubilizing agent, and 1.63 g (0.5 phr relative to reaction solution) of ADK STAB AX-71, available from Adeka Corporation, as an organophosphorus compound were charged and heated to 235° C. to prepare a uniform solution.

The reaction system was depressurized (approximately 3 kPa) so that the boiling point of the reaction solvent became 235° C., TEG-DB and the produced glycolide were codistilled by the heating under reduced pressure, and glycolide was recovered from the codistillation product and obtained. The recovery of the glycolide was performed every hour, and the distillation rate (g/hr) of the glycolide was calculated from the weight of the recovered glycolide. The entire amount of the remaining TEG-DB after the recovery of the glycolide from the codistillation product was refluxed to the flask. During the depolymerization reaction, TGAO in an amount corresponding to the amount of the distilled glycolide was charged every hour.

The depolymerization reaction was performed for 10 hours in the manner described above, and after 10 hours was passed, the reaction temperature was increased to 270° C. by adjusting the pressure to 11 kPa, 1.63 g (0.5 phr) of AX-71 was supplementarily added to further perform depolymerization reaction for 10 hours.

Example 2

A depolymerization reaction of TGAO was performed in the same manner as in Example 1 except for adding, in place of the AX-71, ADK STAB PEP-36, available from Adeka Corporation, every three hours stepwisely in a manner that the accumulated amount was none/0.1/0.3/0.5/1.0 phr and adjusting the reaction solution temperature to 235° C. for the initial 12 hours and 270° C. for the 10 hours thereafter.

Comparative Example 1

A depolymerization reaction of TGAO was performed in the same manner as in Example 1 except for adding no AX-71.

Results of Examples 1 and 2 and Comparative Example 1 are shown in Table 1.

TABLE 1

| | Phosphorus compound | Total distillate amount of crude GL (g/20 hrs) | Purity of crude GL | | Concentration of byproduct in crude GL | | Concentration of Alkali insolubles in reaction solution | |
|---|---|---|---|---|---|---|---|---|
| | | | After 5 hrs (wt. %) | After 20 hrs (wt. %) | After 5 hrs (LCarea %) | After 20 hrs (LCarea %) | After 5 hrs (wt. %) | After 20 hrs (wt. %) |
| Comparative Example 1 | Not added | 335 | 85.4 | 77.6 | 0.61 | 2.66 | 0.6 | 7.2 |
| Example 1 | AX-71 | 186 | 85.8 | 82.4 | 0.25 | 0.92 | 0.4 | 1.6 |
| Example 2 | PEP-36 | 252 | 84.2 | 83.7 | 0.68 | 0.72 | 0.4 | 1.4 |

Table 1 shows the total distillate amount of crude glycolide (GL) produced by the depolymerization reaction, the purities of the crude GL after 5 hours and 20 hours from the start of the depolymerization reaction, the byproduct concentration in the crude GL, and the concentration of alkali insolubles in the depolymerization reaction solution, according to the examples and comparative example of the present invention.

In Table 1, for the total distillate amount of the crude GL, the distillation rate of the glycolide was calculated by recovering the glycolide, which was distilled off continuously, every hour and then measuring the recovered weight. The total distillate amount of the crude GL was the total amount of the distillate amount of the glycolide in the depolymerization reaction for 20 hours. From the results of the total distillate amounts of the crude GL, it was found that the cases where AX-71 and PEP-36 were added tended to lower the distillation rate of the crude GL.

In Table 1, the purity of the crude GL shows the purities of the produced crude glycolide after 5 hours and 20 hours of the depolymerization reaction. Note that the purity of the crude glycolide was measured by gas chromatography. From the results, it was found that the cases where AX-71 and PEP-36 were added suppressed the reduction in the purities compared to the fact that the case where no phosphorus compound was added reduced the purities of the crude GL as the depolymerization reaction time passed.

In Table 1, the byproduct concentration in the crude CL shows the concentration of the byproduct component in the produced crude glycolide after 5 hours and 20 hours from the start of the depolymerization reaction. Note that the byproduct component in the crude glycolide was measured by high-performance liquid chromatography (HPLC). The shown value is the area percentage of the byproduct component peak in the HPLC. From the results, it was found that the cases where AX-71 and PEP-36 were added suppressed increase of the byproduct over time compared to the fact that the case where no phosphorus compound was added increased the concentration of the byproduct component as the depolymerization reaction time passed.

In Table 1, the concentration of the alkali insolubles in the reaction solution shows the concentration of the alkaline insolubles in the depolymerization reaction solution after 5 hours and 20 hours from the start of the depolymerization reaction. The alkali insolubles are thought to become a heavy-component formed from the oligomer in the reaction solution due to heat. Furthermore, a large amount of the alkali insolubles indicates progression of the heavy-component formation from the oligomer in the reaction solution. Note that the concentration of the alkali insolubles was calculated by hydrolyzing the oligomer in the reaction solution by adding an alkali aqueous solution into the depolymerization reaction solution and heating at 90° C. for 4 hrs. recovering the alkali insolubles on a filter paper by filtering the obtained reaction solution, and measuring the weight thereof after drying. From the results, it was found that the cases where AX-71 and PEP-36 were added suppressed increase in the alkali insolubles compared to the fact that the case where no phosphorus compound was added increased the concentration of the alkali insolubles as the depolymerization reaction time passed.

INDUSTRIAL APPLICABILITY

The present invention can be used in a method for producing polyglycolic acid.

The invention claimed is:

1. A method for producing an α-hydroxycarboxylic acid dimeric cyclic ester by subjecting an α-hydroxycarboxylic acid oligomer containing an alkali metal ion to a depolymerization reaction, the depolymerization reaction being performed in the coexistence of an inorganic acid or an inorganic acid salt or a mixture thereof; and an organophosphorus compound; and in the depolymerization reaction, the organophosphorus compound being supplementarily added not earlier than a time when purity of the α-hydroxycarboxylic acid dimeric cyclic ester decreases by 1 wt. % compared to purity at a time when the reaction starts.

2. The method for producing an α-hydroxycarboxylic acid dimeric cyclic ester according to claim 1, wherein the organophosphorus compound is added in an amount of from 0.01 wt. % to 2.0 wt. % relative to an amount of a reaction solution in the depolymerization reaction.

3. The method for producing an α-hydroxycarboxylic acid dimeric cyclic ester according to claim 1, wherein a content of the alkali metal ion is from 0.0001 wt. % to 1.0 wt. % relative to an amount of the α-hydroxycarboxylic acid oligomer.

4. The method for producing an α-hydroxycarboxylic acid dimeric cyclic ester according to claim 1, wherein the organophosphorus compound is a phosphoric acid ester compound.

5. The method for producing an α-hydroxycarboxylic acid dimeric cyclic ester according to claim 1, wherein the α-hydroxycarboxylic acid oligomer is a glycolic acid oligomer.

6. A method for producing a polyglycolic acid, the method comprising:

the method for producing an α-hydroxycarboxylic acid dimeric cyclic ester described in claim 1; and engaging a ring-opening polymerization of the α-hydroxycarboxylic acid dimeric cyclic ester thus produced.

* * * * *